US010058708B2

(12) United States Patent
Zhang et al.

(10) Patent No.: US 10,058,708 B2
(45) Date of Patent: Aug. 28, 2018

(54) HEART FAILURE EVENT DETECTION USING MINIMUM HEART RATE

(71) Applicant: Cardiac Pacemakers, Inc., St. Paul, MN (US)

(72) Inventors: Yi Zhang, Plymouth, MN (US); Viktoria A. Averina, Shoreview, MN (US); Pramodsingh Hirasingh Thakur, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/176,915

(22) Filed: Jun. 8, 2016

(65) Prior Publication Data

US 2017/0001005 A1    Jan. 5, 2017

Related U.S. Application Data

(60) Provisional application No. 62/186,799, filed on Jun. 30, 2015.

(51) Int. Cl.
*A61B 5/00* (2006.01)
*A61N 1/362* (2006.01)
(Continued)

(52) U.S. Cl.
CPC ........ *A61N 1/3627* (2013.01); *A61B 5/02438* (2013.01); *A61B 5/7275* (2013.01); *A61N 1/36535* (2013.01); *A61N 1/36542* (2013.01); *A61N 1/36585* (2013.01); *A61N 1/3702* (2013.01); *A61B 5/4836* (2013.01); *A61B 5/7282* (2013.01)

(58) Field of Classification Search
CPC ... A61B 5/7275; A61B 5/024; A61B 5/02405; A61B 5/02438; A61B 5/4035; A61B 5/4842; A61N 1/3627; A61N 1/36592; A61N 1/3702
See application file for complete search history.

(56) References Cited

U.S. PATENT DOCUMENTS 4,259,966 A    4/1981   Cannon et al.
4,364,397 A    12/1982  Citron et al.
(Continued)

OTHER PUBLICATIONS

Begemann, Malcolm J, et al., "Heart Rate Monitoring in Implanted Pacemakers", Pacing and Clinical Electrophysiology, 11(11), (Nov. 1988), 1687-1693.
(Continued)

*Primary Examiner* — Scott Getzow
(74) *Attorney, Agent, or Firm* — Schwegman Lundberg & Woessner, P.A.

(57) ABSTRACT

Systems, devices, or methods can be used to detect an event, or series of events, that can indicate worsening of congestive heart failure (CHF), or can be used to identify a subject at an elevated risk for developing CHF. A CHF event predictor can be provided using a characteristic minimum of subject cardiac intervals. In an example, the subject cardiac intervals can be obtained during a night-time period or during periods of reduced subject physical activity. A CHF event predictor can be determined using information about physiologic signals received from a subject, such as from a physiologic sensor associated with an ambulatory or implantable medical device.

20 Claims, 10 Drawing Sheets

(51) Int. Cl.
*A61N 1/365* (2006.01)
*A61N 1/37* (2006.01)
*A61B 5/024* (2006.01)

(56) References Cited

U.S. PATENT DOCUMENTS

| | | |
|---|---|---|
| 5,814,087 A | 9/1998 | Renirie |
| 6,045,513 A | 4/2000 | Stone et al. |
| 6,058,328 A | 5/2000 | Levine et al. |
| 6,128,534 A | 10/2000 | Park et al. |
| 6,129,744 A | 10/2000 | Boute |
| 6,438,407 B1 | 8/2002 | Ousdigian et al. |
| 6,599,250 B2 | 7/2003 | Webb et al. |
| 6,636,762 B2 | 10/2003 | Begemann |
| 6,714,811 B1 | 3/2004 | Padmanabhan et al. |
| 6,752,765 B1 | 6/2004 | Jensen et al. |
| 7,313,439 B2 | 12/2007 | Jackson et al. |
| 7,485,095 B2 | 2/2009 | Shusterman |
| 7,558,629 B2 | 7/2009 | Keimel et al. |
| 7,711,415 B1 | 5/2010 | Farazi et al. |
| 7,831,301 B2 | 11/2010 | Webb et al. |
| 7,835,792 B2 | 11/2010 | Lian et al. |
| 7,937,149 B2 | 5/2011 | Stadler et al. |
| 8,036,749 B2 | 10/2011 | Ziegler et al. |
| 8,078,270 B2 | 12/2011 | Webb et al. |
| 8,135,470 B2 | 3/2012 | Keimel et al. |
| 8,175,694 B2 | 5/2012 | Webb et al. |
| 8,255,046 B2 | 8/2012 | Sarkar et al. |
| 8,271,072 B2 | 9/2012 | Houben et al. |
| 8,394,029 B2 | 3/2013 | Lian et al. |
| 8,435,186 B2 | 5/2013 | Hettrick et al. |
| 8,649,864 B2 | 2/2014 | Hastings et al. |
| 8,712,518 B2 | 4/2014 | Kirchner et al. |
| 2005/0124900 A1* | 6/2005 | Stadler ............... A61B 5/0031 600/509 |
| 2005/0256545 A1* | 11/2005 | Koh .................... A61B 5/0031 607/17 |
| 2007/0156057 A1 | 7/2007 | Cho et al. |
| 2009/0043355 A1* | 2/2009 | Cazares ............ A61B 5/0031 607/32 |
| 2010/0030293 A1 | 2/2010 | Sarkar et al. |
| 2010/0298899 A1* | 11/2010 | Donnelly .......... A61B 5/02055 607/6 |

OTHER PUBLICATIONS

Chew, Paul H, et al., "Overnight Heart Rate and Cardiac Function in Patients with Dual Chamber Pacemakers", Pacing and Clinical Electrophysiology, 19(5), (May 1996), 822-828.

Cowie, M. R, et al., "Development and validation of an integrated diagnostic algorithm derived from parameters monitored in implantable devices for identifying patients at risk for heart failure hospitalization in an ambulatory setting", Eur Heart J., 34(31), (Aug. 2013), 2472-80.

Whellan, D. J, et al., "Combined heart failure device diagnostics identify patients at higher risk of subsequent heart failure hospitalizations: results from PARTNERS HF (Program to Access and Review Trending Information and Evaluate Correlation to Symptoms in Patients With Heart", J Am Coll Cardiol., 55(17), (Apr. 27, 2010), 1803-10.

Whellan, D. J, et al., "Development of a method to risk stratify patients with heart failure for 30-day readmission using implantable device diagnostics", Am J Cardiol., 111(1), (Jan. 1, 2013), 79-84.

* cited by examiner

500 →

| | 501 | 502 | 503 |
|---|---|---|---|
| 12AM - 6AM | + + | + + |
| 12AM - 12PM | + + | + |
| 12AM - 6PM | + | 0 |
| 12AM - 12AM (24 HOURS) | + + | 0 |
| 6AM - 12PM | + + | 0 |
| 6AM - 6PM | + | 0 |
| 6AM - 12AM | + | − |
| 12PM - 6PM | − | − − |
| 12PM - 12AM | 0 | − − |
| 6PM - 12AM | 0 | − − |
| | MIN | MEAN |
| | DAY | |

FIG. 5

HEART FAILURE EVENT DETECTION USING MINIMUM HEART RATE

CLAIM OF PRIORITY

This application claims the benefit of priority under 35 U.S.C. § 119(e) of U.S. Provisional Patent Application Ser. No. 62/186,799, filed on Jun. 30, 2015, which is herein incorporated by reference in its entirety.

BACKGROUND

Congestive heart failure (CHF) is a health problem that affects millions of people in the United States alone. CHF generally includes a loss of cardiac efficiency or cardiac output, and can include an inability to provide sufficient blood flow to meet the metabolic demands of peripheral tissues. CHF patients typically have an enlarged heart with weakened cardiac muscles, resulting in reduced contractility and poor cardiac output.

CHF is usually a chronic condition, but can occur suddenly. It can affect the left heart, right heart, or both sides of the heart. When a left ventricle is affected, for example, signals that control the left ventricular contraction can be delayed, or the left and right ventricles may not contract simultaneously. Non-simultaneous contractions of the left and right ventricles can decrease the pumping efficiency of the heart.

OVERVIEW

Frequent monitoring of CHF subjects and timely detection of events indicative of heart failure decompensation can help prevent worsening heart failure, thereby reducing costs associated with hospitalization or rehospitalization. Identifying subjects at an elevated risk for heart failure can help ensure timely treatment, and can improve prognoses and patient outcomes. Identifying and safely managing subjects having a high risk of future heart failure events can avoid unnecessary medical intervention and reduce healthcare costs.

An ambulatory medical device can be used for monitoring CHF subjects and for detecting CHF decompensation events. Examples of such an ambulatory medical device can include an implantable medical device (IMD), a subcutaneous medical device, an implanted or wearable loop recorder, or some other external or wearable medical device. The ambulatory or implantable medical devices can include diagnostic functions, therapy delivery functions, or both. In an example, a device can include one or more physiologic sensors that can be configured to sense electrical or mechanical activity associated with a subject heart, or can be configured to sense a physiologic signal associated with signs or symptoms of worsening heart failure. A medical device can optionally provide a therapy, such as an electrostimulation therapy, to restore or improve cardiac function or neural function. Some devices can provide diagnostics, such as using transthoracic impedance information, heart sound information, electrical signal information, or other information received from a subject body.

Some ambulatory medical devices can include a physiologic sensor configured to detect cardiac interval information, such as heart rate. Other physiologic sensors can be configured to detect heart sounds, cardiac electrical activity, body chemical activity, or other physiologic information. Such information can be used to provide a CHF event predictor metric to aid in diagnostic or therapeutic subject treatment.

Various embodiments described herein can help improve detection or prediction of a CHF event. For example, a system can include an ambulatory medical device (such as an implantable medical device or a wearable medical device) that can provide information about a heart rate trend or determine a CHF event predictor using information about a heart rate. In an example, a characteristic minimum of a subject's heart rate can be used to determine the CHF event predictor. In an example, the characteristic minimum of the subject's heart rate can correspond to a specified time-of-day or subject's sleep/wake state. The characteristic minimum can correspond to a subject's sleep state, or to another period of reduced physical activity level.

In an example, obtaining information indicative of a subject's cardiac interval can include obtaining information about a heart rate that is less than a lower rate pacing limit used by a cardiac rhythm management device that is configured to treat the subject. Obtaining information about a subject's intrinsic heart rate that is less than a lower rate pacing limit can include using systolic or diastolic interval information as a surrogate for heart rate, such as using information about an interval between an R wave (or paced event) and an S2 heart sound.

This Overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 5 illustrates generally an example that can include characteristic heart rate information.

DETAILED DESCRIPTION

Systems, devices, or methods can be used to identify a subject at an elevated risk for developing congestive heart failure (CHF), or can be used to detect an event, or series of events, that can indicate worsening of CHF. In an example, a CHF event predictor can be provided using information about subject cardiac intervals, such as a minimum characteristic of subject cardiac intervals over a specified duration. The CHF event predictor can be determined using information about physiologic signals received from the subject, such as from a physiologic sensor associated with an ambulatory or implantable medical device.

The present inventors have recognized, among other things, that information about a change in a subject heart rate can be used to provide a CHF event predictor. For example, the present inventors have recognized that information about a minimum subject heart rate, such as during a night-time period or during a period of reduced subject physical activity, can provide an indication of worsening CHF. The indication of worsening CHF can be used by a clinician, or used automatically by a device, to update a therapy for the subject, such as to attempt to avert a predicted CHF event by addressing one or more underlying physiologic conditions.

Information about a minimum heart rate can include an indication of an absolute minimum heart rate, or can include some other measure indicative of a minimum characteristic of the heart rate, such as over one or more durations or intervals. In an example, the minimum heart rate can correspond to a minimum of multiple average heart rates, a minimum of multiple mean heart rates, a minimum of multiple intervals or interval averages, or an absolute minimum heart rate. The minimum heart rate can correspond to a minimum among multiple median or average heart rates, a minimum quantitative deviation from some baseline or reference characteristic, or some other measure of one or more of a heart rate or heart activity interval.

In an example, a "minimum heart rate" can be based on a minimum characteristic of a heart rate over multiple separate durations or intervals. For example, a measure (e.g. average, mean, medium, etc.) of the heart rate may be determined for a plurality of durations or intervals (e.g. 5 minutes, 7 minutes, 10 minutes, 15 minutes, 30 minutes, one hour, or other suitable durations or intervals). The measure of the heart rate over the plurality of durations or intervals having the minimum value may then be considered the minimum heart rate. For example, a first average heart rate may be determined over a first 10 minute interval and a second average heart rate may be determined over a second 10 minute interval. The lesser of the first average or the second average may be considered the "minimum heart rate".

Figure 1:
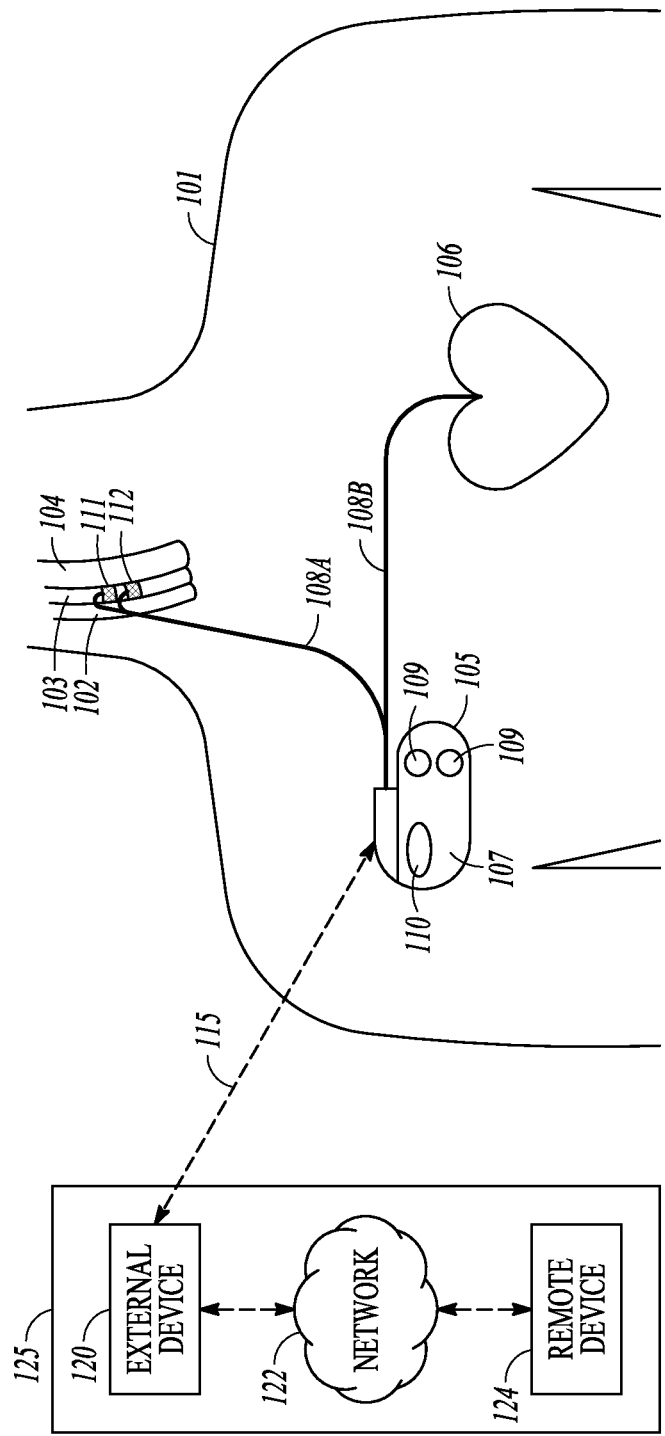
FIG. 1 illustrates generally an example that can include a system that can be configured to provide a congestive heart failure event predictor.

Various systems can be used to generate or provide a CHF event predictor, such as including a system 100 illustrated generally in FIG. 1. The system 100 can include a Cardiac Rhythm Management (CRM) system. The example of FIG. 1 illustrates portions of an environment in which the system 100 can be used. In an example, the system 100 can be configured to determine or use information about a cardiac interval to provide a CHF event predictor for the subject.

The system 100 can include an implantable system that can be used to provide a therapy to a subject and to detect or receive physiologic signal information from the subject, such as including physiologic interval information, impedance information, heart sound information, respiration information, physical activity level information, posture information, physiologic pulsatile signal information, or other information about the subject. In the example of FIG. 1, the implantable system can include an implantable medical device (IMD) 105.

The implantable medical device 105 can be configured to be coupled to one or more of a first implantable lead system 108A and a second implantable lead system 108B. In an example, the first implantable lead system 108A is configured to interact with nerve tissue or cervical vessels in the subject body 101, and the second implantable lead system 108B is configured to interact with cardiac tissue. The implantable medical device 105 can be configured to be coupled to a second medical device wirelessly, such as through an acoustic communication channel or an ultrasonic communication channel. The IMD 105 can be configured to use the subject's physiologic information, such as received from multiple subject sensors, to identify a subject CHF event predictor.

The IMD 105 can include a conductive housing 107 and a processor circuit 110 operably connected to one or more stimulating or sensing circuits. The IMD 105 can be configured to operate autonomously with all circuitry residing within the IMD 105, or the device can be configured to operate with one or more other devices (e.g., other IMD(s) and/or external device(s) such as a programmer or an analyzer circuit). In an example, the IMD 105 can deliver a neural stimulation therapy and can communicate with a different cardiac rhythm management (CRM) device, such as a pacemaker or defibrillator, which can be configured to sense physiological parameter(s) or response(s) and provide a cardiac rhythm management therapy.

In an example, the IMD 105 can include a communication circuit and antenna, or telemetry coil, such as can be used to communicate wirelessly with an external system 125 using a telemetry link 115. The external system 125 can include a remote medical device programmer or one or more other remote external modules (e.g., outside of wireless communication range of the IMD 105 antenna, but coupled to the IMD 105 using an external device, such as a repeater or network access point). The external system 125 can include a dedicated processor circuit configured to process information that can be sent to or received from the IMD 105. The information can include medical device programming information, physiologic data about the subject, device data, instructions, alerts, or other information.

In an example, the external system 125 includes an external device 120 with a user interface configured to display information (e.g., information received from the IMD 105) to a user. The external device can include a local or remote programmer configured to communicate sent or received information to a user or physician, such as including an alert (e.g., via e-mail) about a subject or system 100 status.

The external system 125 can include a patient management system including an external device 120 in proximity of the IMD 105, a remote device 124 in a location relatively distant from the IMD 105, and a telecommunication network 122 linking the external device 120 and the remote device 124. In an example, the external system 125 can include a patient management system that allows access to the IMD 105 from a remote location, such as for monitoring subject status or adjusting a subject therapy or device parameter.

The system 100 can include therapy delivery or information sensing components. For example, the system 100 can include one or more leadless ECG electrodes 109 or other electrodes, such as can be disposed on the housing of the IMD 105. The electrodes can be used to detect physiologic intervals such as corresponding to heart rate, or can detect cardiac arrhythmias, among other characteristics about a subject or about a cardiac cycle. In an example, information received from the leadless ECG electrodes 109 can be analyzed by the processor circuit 110 to identify features of an electrogram, such as to identify fiducials or points of interest on a QRS complex.

In an example, the IMD 105 can be coupled to a first implantable lead system 108A. The first implantable lead system 108A can include at least one neural stimulation lead that can be subcutaneously or intravenously implanted to position electrode(s) to stimulate a neural target in a cervical region (e.g., in a region at or near the neck) in the subject's body 101. Examples of cervical neural targets include a vagus nerve, a carotid sinus nerve, a hypoglossal nerve, a glossopharyngeal nerve, a phrenic nerve, baroreceptors and the nerves that innervate and are proximate to the baroreceptors, and chemoreceptors and the nerves that innervate and are proximate to the chemoreceptors. The neural target may be on the left side (e.g. left vagus nerve), or the right side (e.g. right vagus nerve). Additionally, bilateral neural targets may be stimulated. Other neural stimulation lead(s) can include electrodes configured to stimulate neural targets outside of a cervical region. For example, an electrode can be configured to stimulate a vagus nerve near the stomach.

Implanted electrode(s) disposed proximal to or in contact with a neural target can be used to provide neural electrostimulation. A first electrode 111, such as a first nerve cuff electrode, can be disposed at the end of the neural stimulation lead. In an example, the first electrode 111 can include a nerve cuff electrode that can be sized, shaped, or otherwise configured to be disposed around a vagus nerve 103. One or more additional nerve cuff electrodes, such as a second electrode 112, can be similarly provided. A neural target can be stimulated using at least one electrode positioned internally within a jugular vein 102 or a carotid artery 104. The neural stimulation may be bipolar stimulation or unipolar stimulation, such as where the conductive housing 107 of the IMD 105 functions as an electrode. In an example, neural stimulation may be provided using the first and second electrodes 111 and 112 in a bipolar configuration. In an example, neural or muscular electrical activity can be detected using the first and second electrodes 111 and 112, or an electrical response signal can be provided and/or detected using the first and second electrodes 111 and 112.

In an example, such as shown in FIG. 1, the IMD 105 can be coupled to a second implantable lead system 108B. The second implantable lead system 108B can include a cardiac electrostimulation lead that can be subcutaneously implanted to position one or more electrodes to stimulate cardiac tissue, such as myocardial or neural cardiac tissue. In an example, the second implantable lead system 108B can include multiple atrial and ventricular leads that each includes one or more electrodes for pacing and/or cardioversion/defibrillation. In an example, the IMD 105 can communicate with another electrostimulator wirelessly.

In an example, at least one of the IMD 105 and the external system 125 includes a processor circuit 110 that can be configured to determine or provide a CHF event predictor using at least subject physiologic interval information received using the IMD 105. The processor circuit 110 can analyze and use the CHF event predictor for therapy monitoring, risk stratification, and discharge planning during hospitalization of a heart failure subject, and for monitoring and intervention after the hospitalization of the subject (e.g., in a post-hospitalization or post-episode mode). In some examples, at least a portion of the heart failure analyzer is provided in both the IMD 105 and the external system 125. In an example, the processor circuit 110 can refer to one or more application-specific circuits constructed to perform one or more particular functions, or a general-purpose circuit programmed to perform such function(s). Such a general-purpose circuit includes, but is not limited to, a microprocessor or a portion thereof, a microcontroller or portions thereof, and a programmable logic circuit or a portion thereof, such as can be configured to receive or archive information about the subject received from one or more sensors.

Figure 2:
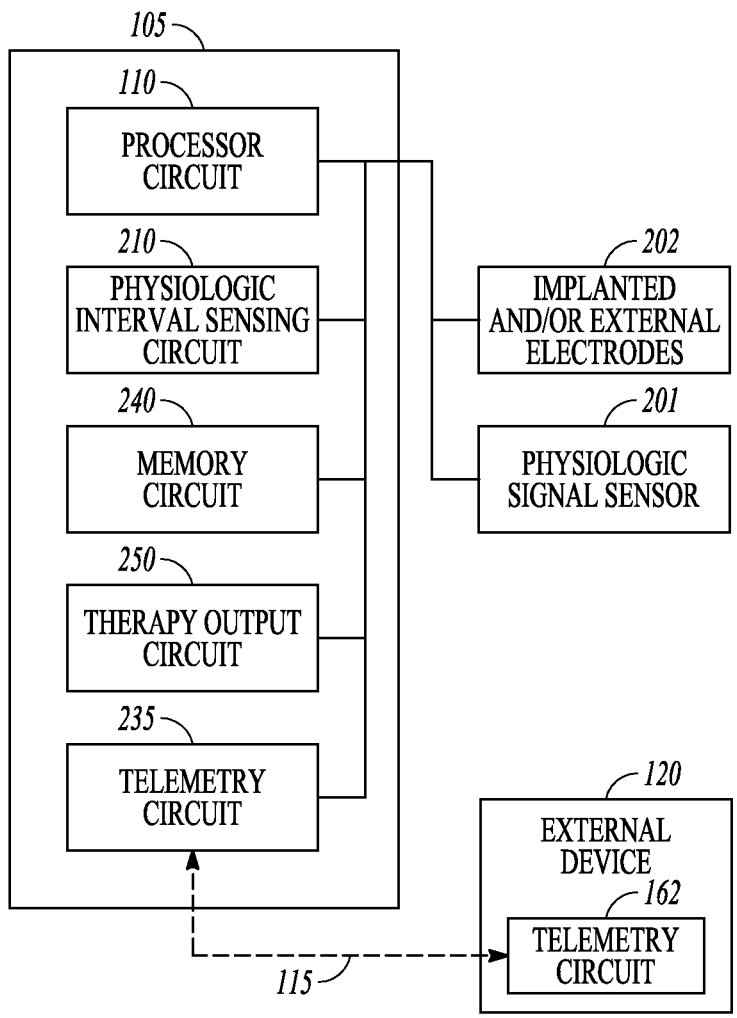
FIG. 2 illustrates generally an example that can include an implantable medical device.

FIG. 2 illustrates generally an example of the IMD 105. The IMD 105 can include the processor circuit 110. The IMD 105 can further include a therapy output circuit 250, such as can be configured to use a current or voltage source to deliver an electrical signal between two or more electrodes (e.g., using one or more electrodes in the first or second implantable lead systems 108A and 108B), such as disposed in a cervical, thoracic, cardiac, or other body region. In an example, the therapy output circuit 250 can be coupled to a neural electrostimulation circuit comprising implanted and/or external electrodes 202 configured to provide electrostimulation to neural targets. In an example, the therapy output circuit 250 is coupled to a cardiac electrostimulation circuit comprising the implanted and/or external electrodes 202 configured to provide electrostimulation in or near a subject heart.

A telemetry circuit 235 can be coupled to the processor circuit 110. The telemetry circuit 235 can transmit data from the IMD 105 to an adjunct system, such as the external device 120. Transmitted data can include, among other things, data from one or more sensors coupled to the IMD 105, diagnostic information generated by the IMD 105, or device configuration or programming information about the IMD 105.

In an example, the processor circuit 110 can be coupled to a physiologic interval sensing circuit 210. The physiologic interval sensing circuit 210 can be configured to receive information about a subject physiologic interval from one or more physiologic sensors using a sensor data input. A subject physiologic interval can include, among other things, a heart rate, a cardiac interval, a heart sound interval, a respiratory interval, an inspiratory interval, and an expiratory interval, or information about a systolic or diastolic interval. The sensor data input can be coupled to one or more of an acoustic sensor, a device-based or other ECG sensor, a vibration sensor, a hemodynamic sensor, a pressure sensor, an activity sensor, an impedance sensor, a respiration sensor, a chemical sensor, a posture sensor, a timer, or other physiologic signal sensor. In an example, the processor circuit 110 includes a data output configured to provide a heart failure parameter about the subject, such as a CHF event predictor or a quantification of a subject's worsening or improving health status. The CHF event predictor can be provided by the processor circuit 110 using information from the physiologic interval sensing circuit 210.

In an example, an acoustic sensor or vibration sensor can be coupled to the processor circuit 110. The sensor can be an implantable or external transducer, such as a microphone or accelerometer. In an example, a portion of the processor circuit 110 can be configured to receive information from the sensor and identify one or more of cardiac interval information such as heart rate, heart sound information, or other physiologic information. In an example, information from the sensor can include acoustic information that can be used to identify an S1 heart sound timing or amplitude characteristic, or to identify a presence of an S3 or S4 heart sound. The sensor can be configured to receive vibrational energy from a subject, such as can be used to identify one or more of cardiac activity, respiratory activity, or other subject physical activity level, such as a relative exercise or exertion level.

In an example, an ECG sensor can be coupled to the processor circuit 110. The ECG sensor can be an implantable or external sensor. For example, the ECG sensor can include at least two electrodes disposed in or on the subject body 101 and configured to detect electrical activity from the subject body 101. The processor circuit 110 can be configured to receive electrogram information from the ECG sensor. In an example, the processor circuit 110 can use the received electrogram information to identify morphological characteristics (e.g., timings, amplitudes, shapes, etc.) of a subject QRS complex, such as to identify a subject heart rate, or to identify a subject R wave timing or a pace event timing.

In an example, a hemodynamic sensor can be coupled to the processor circuit 110. The hemodynamic sensor can be an implantable or external pressure sensor, such as an implantable sensor configured to continuously or intermittently monitor intracardiac or vessel pressures. In an example, the hemodynamic sensor can include a pressure sensor coupled to an RV or atrial lead of the IMD 105, or the hemodynamic sensor 204 can alternatively or additionally include a pressure sensor disposed in a pulmonary artery. The processor circuit 110 can be configured to receive pressure information from the hemodynamic sensor, for example, to determine a subject's heart rate. In an example, information about a subject's hemodynamic status can be used to provide an indication of a subject's heart failure status, such as can be used to initiate other heart failure analyses. For example, a CHF event predictor can be generated in response to heart failure status information received or determined using the hemodynamic sensor.

In an example, an impedance sensor can be coupled to the processor circuit 110. The impedance sensor can be implantable or external to the subject body 101, or can include both implantable and external portions. In an example, the impedance sensor includes at least two electrodes disposed in or on the subject body 101 and configured to detect responsive electrical signals from the subject body 101, such as in response to a non-tissue-stimulating electrostimulation provided to the subject body 101 using the same or different at least two electrodes. In an example, the impedance sensor can include two implanted electrodes (e.g., a can electrode and a remote electrode disposed in or on the heart 106, such as included in the second implantable lead system 108B) in the subject body 101. The processor circuit 110 can be configured to receive electrical signal information from the impedance sensor to identify an impedance between the two or more electrodes. In an example, the processor circuit 110 can use the received impedance information to identify cardiac activity, respiratory activity, muscle activity, thoracic fluid level, a vessel dimensional change (e.g., using impedance plethysmography techniques), or other information about a subject physiologic status, such as including information about a subject's heart rate or other interval indicative of a subject's heart rate. In an example, information from the impedance sensor can be used to provide an indication of a subject's heart failure status, such as can be used to initiate one or more other analyses about a subject's heart failure status. For example, a CHF event predictor can be generated in response to heart failure status information received or determined using the impedance sensor.

In an example, a respiration sensor can be coupled to the processor circuit 110. The respiration sensor can be an implantable or external respiration sensor, such as an implantable sensor configured to monitor a subject's chest expansion and contraction. In an example, the respiration sensor can be configured to provide information about a subject's respiratory rate, tidal volume, breathing patterns, or minute ventilation. In an example, information from the respiration sensor can be used to identify a subject's metabolic status or metabolic demand, such as to identify a period of low exertion or low physical activity level. In an example, information from the respiration sensor can be used to identify a subject's sleep state. In an example, information about a subject's respiration status can be used to provide an indication of a subject's heart failure status, such as can be used to initiate other heart failure analyses. For example, a CHF event predictor can be generated in response to heart failure status information received or determined using the respiration sensor.

In an example, a posture sensor can be coupled to the processor circuit 110. The posture sensor can be an implantable or external posture sensor configured to detect, determine, or differentiate between patient postures. For example, the posture sensor can include an accelerometer configured to provide information about whether the sensor (e.g., installed in or otherwise coupled to the subject) is vertically or horizontally oriented. In an example, the posture sensor can include an impedance sensor, such as configured to measure a thoracic or vessel impedance from which subject orientation can be determined. In an example, information from the posture sensor can be used to identify a sleep state. Information about a subject's posture can be used to provide an indication of a subject's heart failure status, such as can be used to initiate other analyses about a subject's heart failure status. For example, a CHF event predictor can be generated in response to heart failure status information received or determined using the posture sensor.

In an example, at least one other physiologic signal sensor 201 can be coupled to the processor circuit 110 to receive information about a subject physiologic status, such as a subject health status.

In the example of FIG. 2, a memory circuit 240 can be coupled to the processor circuit 110, such as to record subject physiologic information over time. The memory circuit 240 can be configured to receive or store subject cardiac interval or heart rate information over time, such as in a histogram or other data storage format. In an example, the processor circuit 110 can access subject physiologic information stored in the memory circuit 240, such as to identify a change or trend in the subject's physiologic information over time.

In an example, subject cardiac interval information can be stored in the memory circuit 240 and trended over time using the processor circuit 110, such as to identify a subject's increasing or decreasing heart rate over time. In an example, the processor circuit 110 can be configured to identify a cardiac interval trend over a specified data collection window, such as further described herein. Information about the cardiac interval trend can be provided to a clinician using a user interface of the external device 120. In an example, the information about the cardiac interval trend is provided together with one or more visual indications to help the clinician to interpret the trend information. For example, a cardiac interval trend can be displayed together with regions indicated or understood to mean "safe" or "unsafe". The regions can be visually distinguished using shading or some other visual differentiation technique. The regions can correspond to ranges of normal and abnormal values. When a trend departs or trends away from a safe region, or approaches or enters an unsafe region, the visual display indications can help to enhance a visual distinction of worsening versus normal fluctuations in the signal. A region boundary can be computed as a fixed value, or a boundary can be a function of the signal itself. Additionally or alternatively, a region boundary can be based on contextual information determined using one or more other trends (e.g. in the presence of AF, a "safe" zone boundary can be updated). A region boundary can be programmed or adjusted manually by a clinician.

A user interface can additionally or alternatively provide a numerical or quantitative indication of a cardiac interval or cardiac interval trend relative to a reference such that the clinician can identify a change in the subject's health status. In an example, the trend and/or the numerical or quantitative indication can be used by a clinician (or other processor circuit, such as in a remote patient management system) to determine a CHF event predictor.

In an example, the systems described above in the discussion of FIGS. 1 and 2, such as including the external system 125 and the IMD 105, among other systems, can be used to monitor or receive physiologic signals from a subject using one or more subject physiologic sensors. The external system 125 or the IMD 105 can be configured to identify or receive an indication of a first duration that corresponds to a reduced subject physical activity level or to an expected subject sleep period. The external system 125 or the IMD 105 can be configured to receive information indicative of one or more cardiac intervals corresponding to the first duration, for example, to identify a characteristic minimum. In an example, a characteristic minimum can include a minimum subject heart rate or a lower percentile subject heart rate over the first duration. The characteristic minimum can be used to determine a subject CHF event predictor, such as using the processor circuit 110 or other processor in the system 100.

In an example, a subject CHF event predictor can be used to identify worsening heart failure and, depending on the sensors used to determine the heart failure parameter, various subject therapies can be initiated or adjusted, such as automatically by the processor circuit 110. In an example, in response to a CHF event predictor that indicates worsening heart failure, a lower rate limit of the IMD 105 can be raised, such as temporarily to alleviate symptoms. In an example, in response to worsening heart failure, a pacing amplitude or pacing waveform shape can be changed. For example, an amplitude can be increased, or a duration of one or both portions of a biphasic waveform can be increased or decreased. In an example, in response to worsening heart failure, an electrostimulation application location can be changed. For example, using a multipolar lead, different combinations of electrodes (e.g., corresponding to a left ventricle) can be selected.

In an example, heart rate can be measured by identifying a time interval between a sensed depolarization of a subject heart chamber and a preceding sensed depolarization or electrostimulation (e.g., pacing) event. The time interval can be measured using information about ventricular or atrial subject cardiac activity. In an example, multiple intervals can be measured over a specified period, and a characteristic of the multiple intervals can be recorded or used for further analysis. In an example, the characteristic can include a maximum, minimum, mean, median, standard deviation, percentiles, quartiles, or other characteristic of the multiple intervals. In an example, the characteristic can include a most frequent interval, such as can be determined using a histogram of measured intervals.

In an example, cardiac intervals can be measured over successive or adjacent time periods, such as using the IMD 105, or successive average values of cardiac intervals can be measured over discontinuous time periods. Discontinuous time periods can be selected (e.g., automatically or by a user) to correspond to a particular time of interest, for example, during the night or day, or to correspond to a specified subject physiologic status. In an example, cardiac interval information can be received using the physiologic interval sensing circuit 210 during a night-time period when a subject is likely to be sleeping or resting. For example, the cardiac interval information can be received using the physiologic interval sensing circuit 210 between about midnight (12 AM) and 6 AM.

The present inventors have recognized, among other things, that a problem to be solved can include identifying a subject characteristic for improved identification or monitoring of heart failure patients. The present subject matter can provide a solution to this problem, such as by using subject cardiac interval information, or heart rate information, corresponding to a specified time-of-day. For example, the present inventors have recognized that particular characteristics of cardiac interval information, such as corresponding to a particular time-of-day, can be used to provide a congestive heart failure event predictor. The congestive heart failure event predictor can be used as a warning to a subject or a clinician that a heart failure event is more likely, or that a subject's therapy should be changed.

For example, the present inventors have recognized that subject heart rate during sleep, or during periods of reduced subject physical activity level, can be controlled by the subject parasympathetic nervous system, and that heart failure can generally be associated with an increase in night-time heart rate, such as due to improper excitation of the parasympathetic nervous system. The present inventors have further recognized that day-time heart rate can be controlled by the subject sympathetic nervous system, and that a difference between day-time and night-time heart rate can indicate autonomic dysfunction or indicate a subject risk for heart failure.

Figure 3:
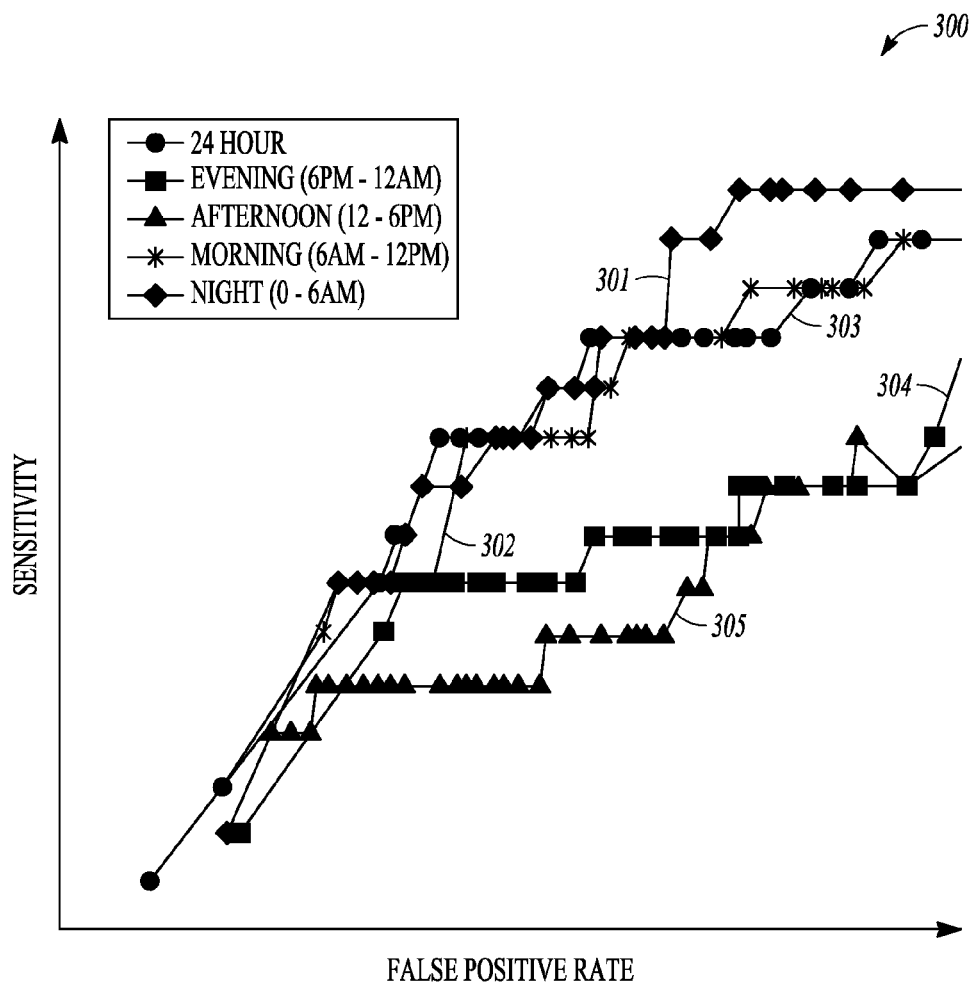
FIG. 3 illustrates generally an example that can include receiver operating characteristic curves corresponding to characteristics of a subject's cardiac interval data.

FIG. 3 illustrates generally an example 300 that can include receiver operating characteristic (ROC) curves corresponding to various characteristics of cardiac interval data collection periods for a subject. In an example, a heart rate interval trend can be determined as a difference between a first characteristic or statistical measure from multiple interval measurements within a first time period or first time window, and a second characteristic or statistical measure from multiple interval measurements within a second time period or second time window. The first and second characteristics or statistical measures can each include a mean, median, percentile, quartile, minimum, maximum, range, standard deviation, or other measure of central tendency and/or spread of the signal values in a respective one of the time windows, such as further described below in the example of FIG. 6. In an example, at least one of the characteristics or statistical measures can indicate a cardiac interval baseline, such as a subject-specific cardiac interval baseline.

In the example 300 of FIG. 3, the ROC curves can illustrate generally a performance of a detector or of a detection algorithm for determining whether a particular signal indicates an increased likelihood of a CHF event. The ROC curves depict generally the sensitivity of detecting the likelihood of the CHF event (shown on the y-axis) over the corresponding patient-per-year false positive rate (shown on the x-axis) for multiple detection thresholds.

The example 300 includes multiple ROC curves that correspond to different cardiac interval detection periods or data collection time windows. A first ROC curve 301 corresponds to an early morning period, such as from 12 AM to 6 AM. A second ROC curve 302 corresponds to a morning period, such as from 6 AM to 12 PM. A third ROC curve 303 corresponds to a 24 hour (full day) period. A fourth ROC curve 304 corresponds to a night period, such as from 6 PM to 12 AM. A fifth ROC curve 305 corresponds to an afternoon period, such as from 12 PM to 6 PM.

For a specified false positive rate, a higher sensitivity can generally correspond to the ROC curves 301, 302, and 303. That is, a higher sensitivity can generally correspond to a cardiac interval detection period that includes at least early morning or morning times. Lower sensitivity can generally correspond to the ROC curves 304 and 305. Each of the ROC curves 304 and 305 excludes early morning or morning times.

In an example, an area under an ROC curve (AUC) can provide an index that can be used to evaluate a particular detector's performance. A qualitative comparison of the ROC curves 301-305 in the example 300 shows that the AUC of the first ROC curve 301 is greater than the AUC of the other curves 302-305. Therefore, in the context of detecting events most likely to lead to a CHF event, the example shown in FIG. 3 suggests that the representative cardiac interval information received over the early morning time window outperforms cardiac interval information received over other intervals.

Figure 4:
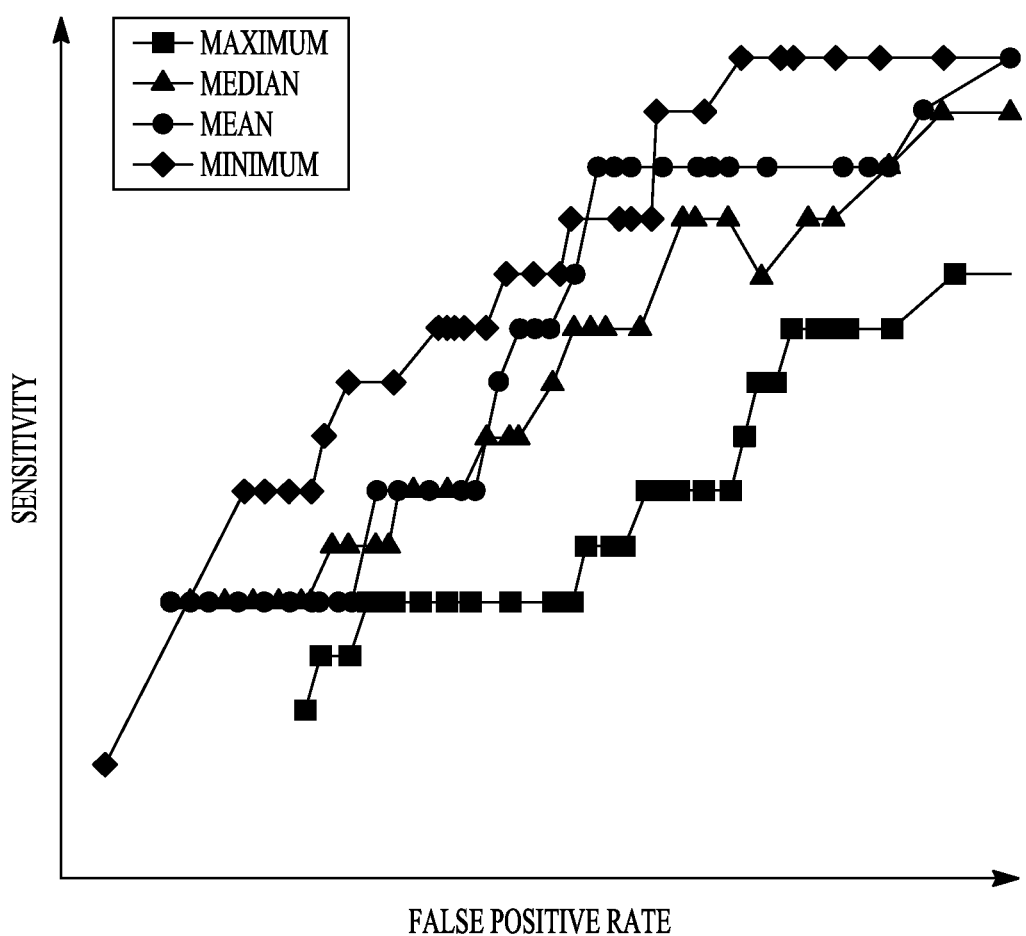
FIG. 4 illustrates generally an example that can include receiver operating characteristic curves corresponding to characteristics of a subject's cardiac interval data.

FIG. 4 illustrates generally an example 400 that includes receiver operating characteristic (ROC) curves corresponding to various characteristics of subject cardiac interval data. In an example, an interval trend can be determined as a difference between a first characteristic or statistical measure from multiple interval measurements within a first period or first time window, and a second characteristic or statistical measure from multiple interval measurements within a second period or second time window. The first and second characteristics or statistical measures can each include a mean, median, percentile, quartile, minimum, maximum, standard deviation, range, or other measure of central tendency and/or spread of the signal values in a respective one of the time windows, such as further described below in the example of FIG. 6. In an example, at least one of the characteristics or statistical measures can indicate a cardiac interval baseline, such as a subject-specific cardiac interval baseline.

In the example 400 of FIG. 4, the ROC curves can illustrate generally a performance of a detector or of a detection algorithm for determining whether a particular signal indicates an increased likelihood of a CHF event. As in the example of FIG. 3, the ROC curves in FIG. 4 depict generally the sensitivity of detecting the likelihood of the CHF event (shown on the y-axis) over a corresponding patient-per-year false positive rate (shown on the x-axis) for multiple detection thresholds.

The example 400 includes multiple ROC curves that correspond to different characteristics of subject cardiac interval data, such as obtained over a common time window. A first ROC curve 401 corresponds to a minimum heart rate (or maximum interval). A second ROC curve 402 corresponds to an average or mean heart rate. A third ROC curve 403 corresponds to a median heart rate. A fourth ROC curve 404 corresponds to a maximum heart rate (or minimum interval).

For a specified false positive rate, a higher sensitivity can generally correspond to the ROC curve 401. That is, a higher sensitivity can generally correspond to a minimum heart rate (or maximum interval) characteristic of subject cardiac interval data. Lower sensitivity can generally correspond to the ROC curves 402-404. The fourth ROC curve 404, corresponding to a maximum characteristic of subject heart rate, has a particularly low sensitivity for detecting the likelihood of a CHF event.

A qualitative comparison of the ROC curves 401-404 in the example 400 shows that the AUC of the first ROC curve 401 is greater than the AUC of the other curves 402-304 shown. Therefore, in the context of detecting events most likely to lead to a CHF event, the example shown in FIG. 4 suggests that the minimum heart rate characteristic (or maximum cardiac interval characteristic) can outperform some other characteristics or metrics, including at least mean, median, and maximum heart rate characteristics.

FIG. 5 illustrates generally an example 500 of minimum and mean heart rate characteristic information for multiple different time windows. The example 500 can correspond to a sensitivity at a false positive rate of about 1.5 patients per year. In the example of FIG. 5, the first column 501 indicates different data collection time periods. The second column 502 indicates qualitative characteristic minimum heart rate information (maximum cardiac interval information) for each of the different time periods. The third column 503 indicates qualitative characteristic mean heart rate information (mean cardiac interval information) for each of the different time periods.

In the example 500 of FIG. 5, "+", "−", and "0" are used to indicate relative sensitivities of the minimum heart rate and mean heart rate characteristics corresponding to the different time periods. For example, the first and second rows of the second column 502 show "++" for each of the 12 AM-6 AM and 12 AM-12 PM time periods. The third row of the second column 502 shows "+" for the 12 AM-6 PM time period. Therefore, the first and second rows of the second column 502 indicate that the minimum heart rate, such as measured during either the 12 AM-6 AM or 12 AM-12 PM time windows, corresponds to a higher sensitivity than the minimum heart rate measured during the 12 AM-6 PM time window (row 3). Generally, the periods including night or morning hours (e.g., rows 1-7) show a relatively higher sensitivity than the others. In the example 500, the characteristic minimum heart rate indicates a higher sensitivity for any given time period as compared to the characteristic mean heart rate.

Figure 6:
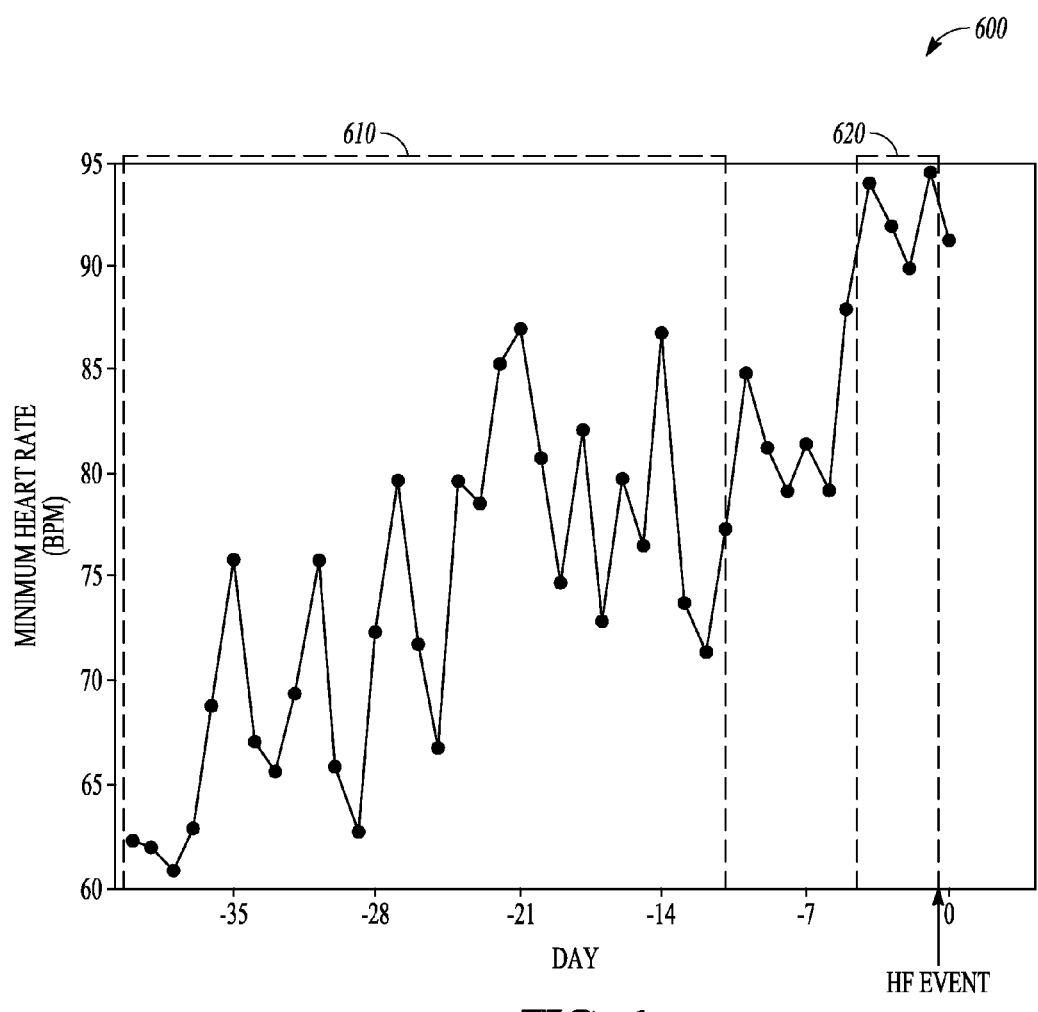
FIG. 6 illustrates generally an example that can include using multiple time windows to provide a congestive heart failure event predictor.

FIG. 6 illustrates generally an example 600 that can include using multiple time windows to determine a signal that can be used to provide a CHF event predictor. The example 600 includes a chart showing a minimum heart rate in BPM on the y-axis, and a time or day indication on the x-axis. For each of the forty days shown, a minimum heart rate characteristic can be plotted on the chart. Heart rate information used to determine the CHF event predictor can be associated with one or more of the time windows.

In an example, a characteristic minimum of the example 600 can be used to provide the CHF event predictor. A characteristic minimum can include a minimum subject heart rate, such as acquired over a specified duration. The characteristic minimum can correspond to cardiac interval information received using the physiologic interval sensing circuit 210 over a duration that can correspond to a period of reduced or minimum subject physical activity level, such as a subject sleep period. In an example, subject cardiac interval information can be collected in response to an indication of a subject sleep period.

In an example, a characteristic minimum can include information about multiple cardiac cycles (e.g., to reduce signal noise). For example, minimum heart rate information at a present-day (e.g., corresponding to "0" on the x-axis in the example of FIG. 6) can include an average of all measured cardiac intervals over a specified duration, such as corresponding to a subject sleep period. In an example, one or more samples of the cardiac interval information obtained during the multiple cardiac cycles can be discarded, such as absolute minima or maxima, such as can represent noise under some circumstances. In the example of FIG. 6, the minimum heart rate information at day 0 can be about 91 BPM, such as corresponding to an average of multiple cardiac interval samples over an n-minute (or second, hour, etc.) measurement period, such as corresponding to a subject sleep period.

In an example, a period corresponding to a subject sleep state can include 12 AM-1 AM. This one hour period can optionally be further divided, such as into 20 minute measurement periods. That is, 12 AM-1 AM can be divided into three time periods, including 12:00 AM-12:20 AM, 12:20 AM-12:40 AM, and 12:40 AM-1:00 AM. Subject cardiac interval information can be sensed or recorded during each of the three time periods, such as using the physiologic interval sensing circuit 210 or the memory circuit 240. In an example, a characteristic of the subject cardiac interval information can be determined for each of the three time periods. For example, an average minimum heart rate can be calculated for each of the three time periods. The lowest minimum heart rate among those measured for the various time periods can be recorded, such as in a chart as in the example of FIG. 6. Other data points in the example 600 can similarly correspond to an average of multiple cardiac interval samples over respective 20 minute (or differently dimensioned) measurement periods.

In the example of FIG. 6, day 0 can correspond to a CHF event, such as a decompensation event. A short-term window 620 can correspond to the several days leading up to the CHF event. In the example of FIG. 6, the short-term window 620 includes 4 days, labeled day "−1" through day "−4". A long-term window 610 can correspond to a subject baseline, or can correspond to a longer period leading up to the CHF event. In an example, information about a likelihood of a CHF event can be identified using a signal determined using a characteristic or statistical measure of the data corresponding to the short-term or long-term windows 620 or 610. A characteristic or statistical measure of cardiac interval information for a particular window can include an average, mean, minimum, maximum, median, standard deviation, or other measure of one or more data points in the window.

In an example, a signal used to provide information about a likelihood of a CHF event can include a difference between an average of the cardiac interval information in the long-term window 610 and an average of the cardiac interval information in the short-term window 620. When the difference exceeds a specified threshold, the data in the short-term window 620 can indicate a rising heart rate (e.g., due to abnormal activation of the parasympathetic nervous system) relative to the data in the long-term window 610, or relative to a baseline. Under these conditions, for example, an indication of an increased risk for a CHF event can be provided, such as using the processor circuit 110 and one of the external device 120 or the remote device 124. In an example, a signal can include a normalized difference, such as a difference between an average of the cardiac interval information in the long-term window 610 and an average of the cardiac interval information in the short-term window 620, such as normalized by an average of the cardiac interval information in the long-term window 610, or by a baseline value. The signal can optionally include a percentage difference or relationship between the data in the long-term and short-term windows 610 and 620.

In an example, a signal used to provide information about a likelihood of a CHF event can include a slope of a cardiac interval data set, such as corresponding to all or a portion of the data in the example 600. A slope can be based on a regression line, such as can be calculated using cardiac interval data from one or more days. In an example, when the slope exceeds a specified threshold, such as to indicate a rising subject heart rate (e.g., corresponding to a night-time or early morning-time interval), a CHF event predictor can include an indication of an increased likelihood of a subject CHF event.

In an example, a signal used to provide information about a likelihood of a CHF event can include slope information about the data set overall, about the data in the short-term window 620, or about the data in the long-term window 610. In an example, slopes corresponding to each of the long-term window 610 and the short term window 620 data can be compared, and the results of the comparison can be used to provide a CHF event predictor. For example, when a slope corresponding to data in the short-term window 620 exceeds a slope corresponding to data in the long-term window 610, a CHF event predictor can indicate an increased likelihood of a subject CHF event.

Cardiac interval information about a subject can be collected over a period that corresponds to a subject sleep state or a subject reduced physical activity level. A period corresponding to a subject sleep state or a subject reduced physical activity level can be identified, such as using the processor circuit 110, using one or more of time of day information, information from one or more physiologic or environment sensors, or information from a subject or clinician. In an example, subject cardiac interval information can be collected over a similar period each day, such as when a subject is expected to be sleeping or resting. For example, the subject cardiac interval information can be collected over a night-time period including 12 AM through about 6 AM. The data collection period start time, end time, or duration can be adjusted, such as by a subject or clinician input.

In an example, subject cardiac interval information can be collected in response to a detected or determined subject sleep state. A subject sleep state can be identified using information from one or more of an activity level sensor or accelerometer, a posture sensor, a heart rate sensor, a heart rate variability sensor, or a respiration sensor. Information from the one or more sensors can be used to identify a subject metabolic demand, such as can be used to identify a subject sleep state. In an example, subject cardiac interval information can be collected in response to a subject or clinician input that can indicate the subject plans to sleep or is already sleeping.

The present inventors have recognized that a problem to be solved can include using information about a subject cardiac interval when the subject receives an electrostimulation therapy that includes a maximum electrostimulation interval limit, or a lower rate pacing limit. For example, the problem can include using subject heart rate information at or below a lower rate pacing limit that is enforced by a cardiac rhythm management or other device. In an example, the problem can include identifying an increase in a minimum subject heart rate at or near the lower rate pacing limit, and determining whether the heart rate increase at or near the lower rate limit can indicate a likelihood of a CHF event.

The present inventors have recognized that a solution to this problem can include using information about a subject systolic interval. In an example, even in the presence of a lower rate pacing limit therapy, information about a systolic interval can indicate an underlying sinus rhythm. In an example, the present application can additionally or alternatively provide a solution to the problem, such as by providing a hysteresis search function to identify information about a sinus or intrinsic cardiac interval.

In an example, a hysteresis search function can be used to temporarily suspend a maximum electrostimulation interval limit. During the suspended interval limit, the processor circuit 110 can receive subject cardiac interval information. The suspension duration can correspond to a sensing period of interest, such as a night-time sensing period. In an example, the processor circuit 110 can configure the IMD 105 to transiently reduce a lower rate pacing limit therapy from a first rate limit to a lesser rate limit (that is, to a larger maximum interval between intrinsic contractions before the IMD 105 automatically intervenes). In an example, the hysteretic search function can be configured to intermittently reduce the lower rate pacing limit multiple times over the sensing period of interest. Sensed cardiac interval information during the period of interest can be averaged to generate a signal that can be used to provide an indication of a likelihood of a CHF event, such as described above.

In an example, the hysteresis search function can be initiated in response to a received indication of worsening heart failure. A worsening heart failure indication can include, among others, a change in a subject thoracic impedance, a change in a subject S1 or S3 heart sound characteristic, a low subject physical activity level, or an increase in subject atrial fibrillation burden. In an example, a worsening heart failure indication can include information about a subject respiratory status, such as a change in subject breathing pattern, including an increase in a subject respiratory rate, a decrease in tidal volume, an increase in rapid shallow breathing, or an increase in frequency of apnea or hypopnea episodes.

In an example, the hysteresis search function can be initiated intermittently during a time window of interest, such as to establish a baseline heart rate. The hysteresis search can be performed for a specified duration each day (e.g., during a nighttime interval), for a specified duration over multiple days, or for a specified duration in response to a detected event (e.g., a duration following a detected heart rate at the LRL). In an example, a hysteresis search can be initiated when a subject's HR stays at a LRL for a specified duration. For every x minutes that a subject's HR is at the LRL, the LRL floor can be lowered for a brief period, such as several seconds, to obtain information about the subject's sinus HR.

Additionally or alternatively to the hysteresis search function, in an example, information about a subject systolic interval can be used to indicate an underlying intrinsic or sinus cardiac interval, such as when a lower rate limit therapy is provided to the subject. In an example, the systolic interval can include an R-S2 interval. An R-S2 interval can include an interval from an R wave of a QRS complex (e.g., an R wave peak, an R wave onset, a pace event, or other characteristic corresponding to an R wave timing) to an S2 heart sound (e.g., an S2 peak amplitude, an S2 onset, or other characteristic corresponding an S2 timing). In response to a cardiac electrostimulation event, such as a pace event, a portion of a cardiac cycle can occur under autonomic drive. In an example, an R-S2 interval can be determined using a timing associated with the electrostimulation event as the R wave portion of the interval.

Figure 7:
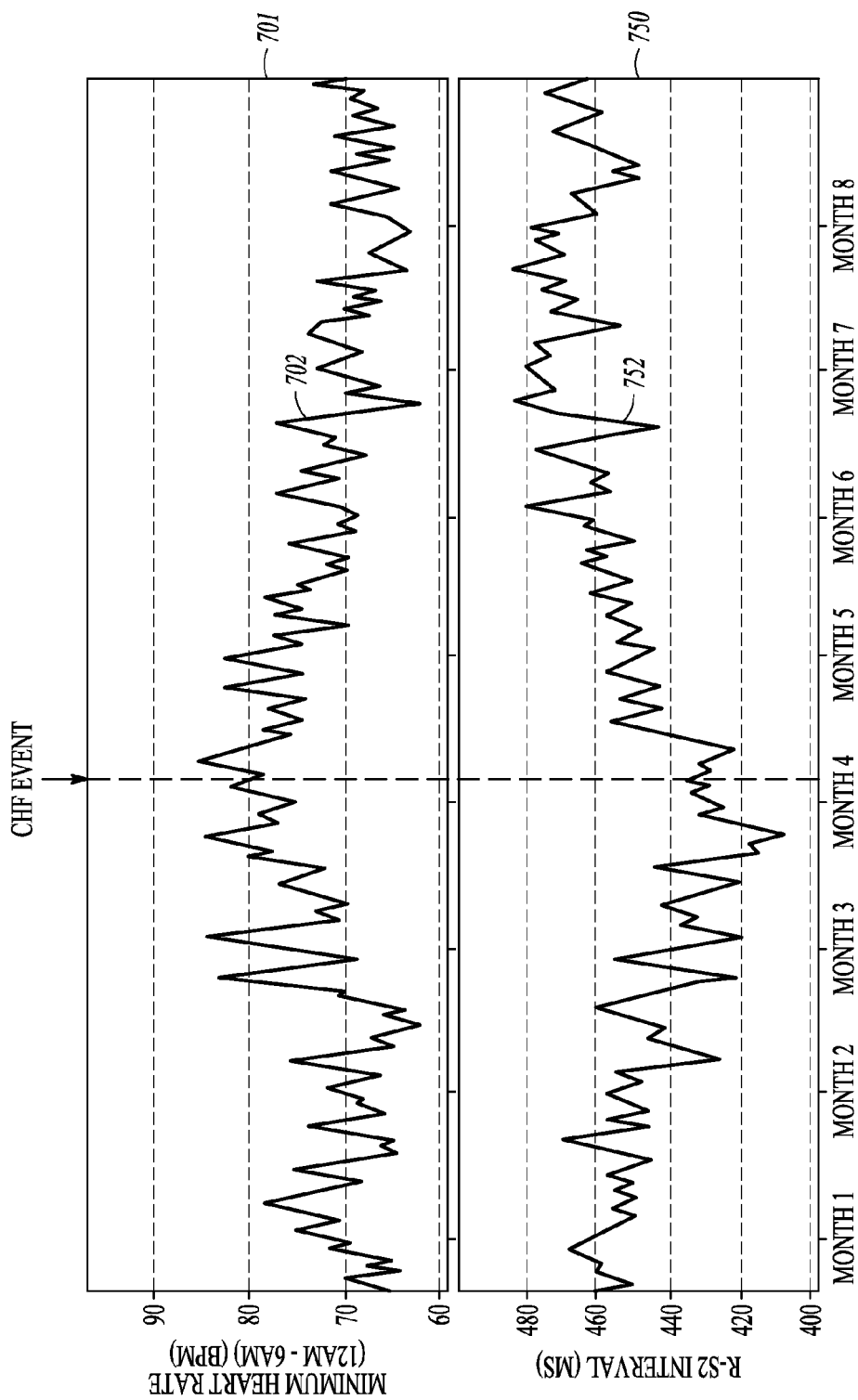
FIG. 7 illustrates generally an example that can include heart rate information, R-S2 interval information, and a congestive heart failure event.

FIG. 7 illustrates generally an example of heart rate information and R-S2 interval information before and after a CHF event. In the example of FIG. 7, a first heart rate chart 701 includes a first heart rate trendline 702 that can indicate a subject heart rate over an extended period. The first heart rate trendline 702 can include, for example, daily or weekly measures of a subject minimum heart rate, such as can be acquired or received in the manner described above in the discussion of FIGS. 1-6. The first heart rate trendline 702 indicates generally that the subject minimum heart rate increased from a baseline of about 65 BPM to about 81 BPM over a period preceding the CHF event. Following the CHF event, the subject minimum heart rate can trend toward the subject baseline rate.

The example of FIG. 7 includes a first R-S2 interval chart 751 that can include a first R-S2 interval trendline 752. The first R-S2 interval trendline 752 can include, for example, daily or weekly measures of a subject R-S2 interval information, such as can correspond to the measures of the subject minimum heart rate used to generate the first heart rate trendline 702. For example, measurements of the subject R-S2 interval can occur concurrently or near-in-time to the measurements of the subject minimum heart rate.

The first R-S2 interval trendline 752 can be generated using information from, among other sources, the IMD 105, the processor circuit 110, the therapy output circuit 250, the implanted and/or external electrodes 202, or the physiologic signal sensor 201. The first R-S2 interval trendline 752 indicates generally that the subject R-S2 interval decreased from a baseline of about 460 msec to about 420 msec over a period preceding the CHF event.

Taken together, the first heart rate trendline 702 and the first R-S2 interval trendline 752 show an approximately linear, inverse relationship between minimum heart rate and R-S2 interval. Under some circumstances, information about R-S2 can be used as a surrogate for minimum heart rate. In the example of FIG. 7, following the CHF event, the first heart rate trendline 702 decreases to an approximately normal or baseline level, and, inversely, the first R-S2 interval trendline 752 increases to an approximately normal or baseline level.

Figure 8:
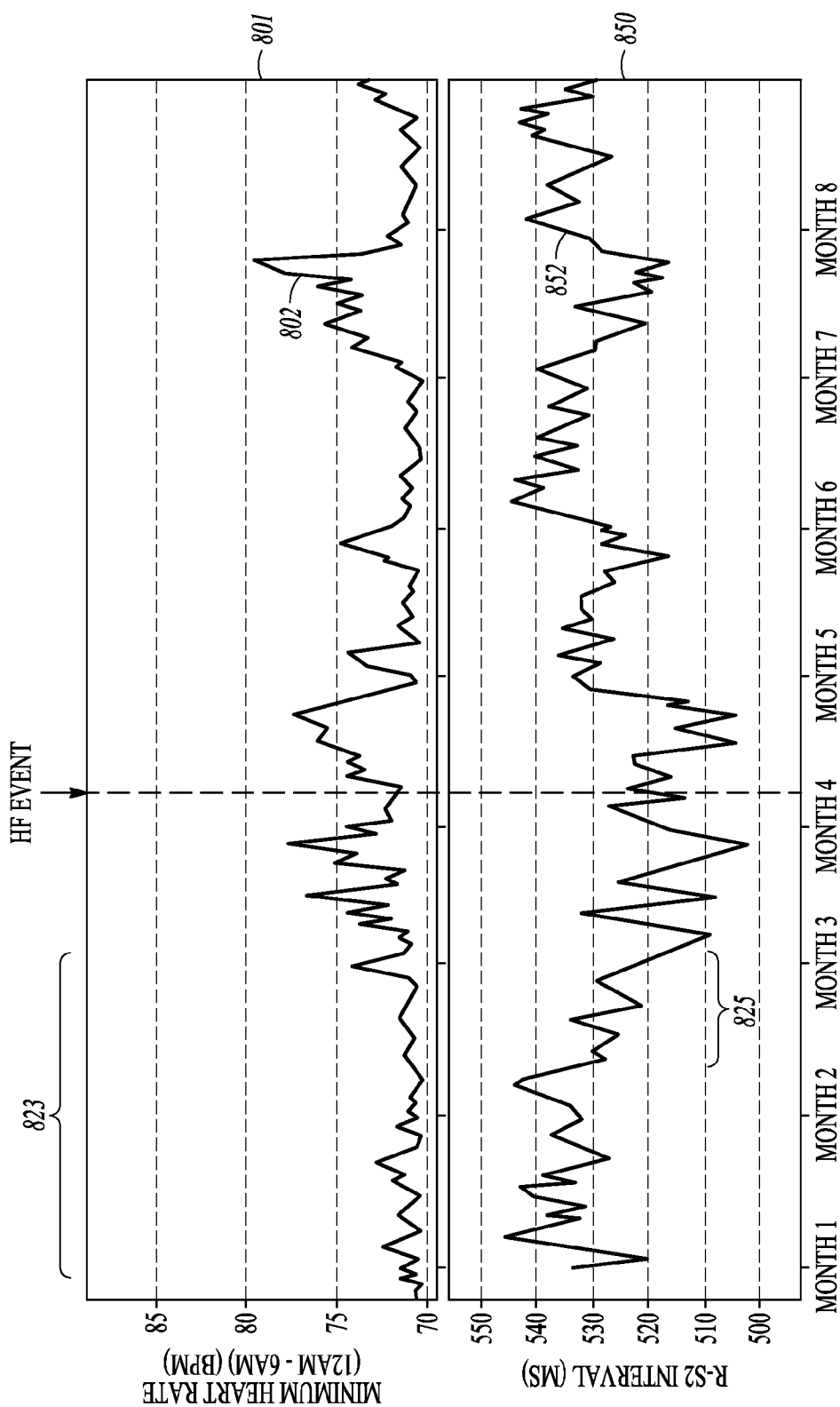
FIG. 8 illustrates generally an example that can include heart rate information, R-S2 interval information, and a congestive heart failure event.

FIG. 8 illustrates generally an example of heart rate information and R-S2 interval information before and after a CHF event, such as for a subject receiving an electrostimulation therapy at LRL. In the example of FIG. 8, the electrostimulation therapy can be configured to provide the subject with an electrostimulation whenever a specified maximum interval is exceeded without intrinsic cardiac activity. That is, the electrostimulation therapy can include a lower rate pacing limit, or lower rate limit (LRL).

In the example of FIG. 8, a second heart rate chart 801 can include a second heart rate trendline 802 that can indicate a subject heart rate over an extended period. The second heart rate trendline 802 can include, for example, daily or weekly measures of a subject minimum heart rate, such as can be acquired or received in the manner described above. The second heart rate trendline 802 indicates generally that the subject minimum heart rate increased from about 71 BPM to about 74 BPM over a period preceding the CHF event.

In the example of FIG. 8, a first period 823 can include a period during which the subject can receive a lower rate limit therapy, such as from the IMD 105. The therapy can be provided such that the subject minimum heart rate generally cannot fall below a specified threshold, such as 71 BPM in the example of FIG. 8. Leading up to the CHF event, however, the subject minimum heart rate can exceed the specified threshold, and an increase in minimum heart rate can be detected. However, as shown in the example of FIG. 8, the increase in minimum heart rate can be small. The present inventors have recognized that a problem to be solved can include identifying when even a slight increase in minimum heart rate can be considered to be indicative of an impending CHF event or an increased subject risk for a CHF event.

The present inventors have recognized that systolic interval information, such as R-S2 interval information, can be used as a surrogate for subject minimum heart rate information, such as even when a subject receives a lower rate pacing limit (or similar) therapy. The example of FIG. 8 includes a second R-S2 interval chart 851 that can include a second R-S2 interval trendline 852. The second R-S2 interval trendline 852 can include, for example, daily or weekly measures of a subject R-S2 interval, such as can correspond to the subject minimum heart rate information in the second heart rate trendline 802. The second R-S2 interval trendline 852 indicates generally that the subject R-S2 interval decreased from a baseline of about 535 msec to about 510 msec over a period of several weeks preceding the CHF event.

The second R-S2 interval trendline 852 indicates generally that the subject R-S2 interval can decrease from a baseline when the subject heart rate is maintained by an electrostimulation therapy, such as a lower rate limit therapy. In the example of FIG. 8, the first period 823 can include a period during which the subject can receive the lower rate limit therapy, and a second period 825 can include a portion of the first period 823 when the minimum subject heart rate would be expected to rise but for the active lower rate limit therapy. For example, although a sinus or intrinsic subject heart rate can be masked by the lower rate limit therapy, information about a subject R-S2 interval can be used as a surrogate to reveal or provide information about an expected corresponding minimum subject heart rate. When the R-S2 interval indicates the minimum subject heart rate is increasing, such as in the presence of a lower rate limit therapy, an alert can be provided to a subject or to a clinician that the subject can be at an elevated risk for an adverse heart failure event.

In an example, in response to an indication of an increased likelihood of an adverse CHF event, a subject therapy can be updated or a device parameter can be updated, such as manually by a subject or a clinician, or automatically by the IMD 105 or by another component of the system 100. Updating a subject therapy can include adjusting one or more of an AV delay interval, a VV delay interval, a lower rate pacing limit, an electrostimulation amplitude threshold, an LV pacing electrode configuration (e.g. using quadrapolar leads), or changing a pacing mode, such as to or from a mode that is rate-responsive or activity-responsive, or to or from a forced atrial pacing mode. Some examples of other device parameters that can be optimized can include a pacing voltage, or a pacing pulse width, or a pacing pulse shape, among others.

Figure 9:
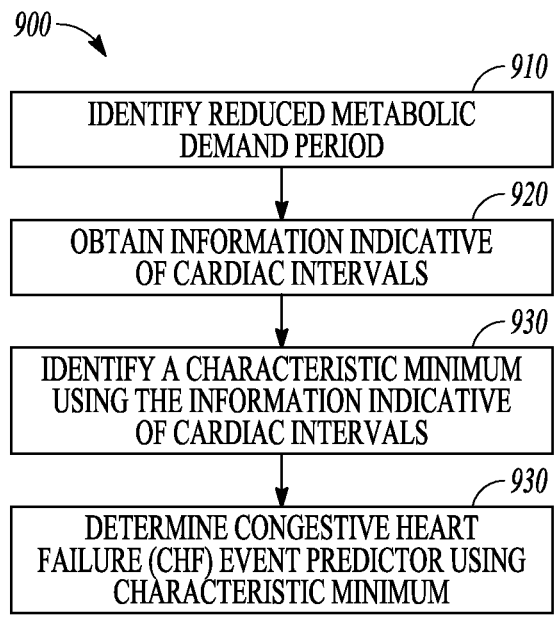
FIG. 9 illustrates generally an example that can include determining a congestive heart failure event predictor.

Various methods can include determining or using a congestive heart failure (CHF) event predictor. For example, FIG. 9 illustrates generally an example 900 that can include determining a CHF event predictor using information about a subject characteristic minimum heart rate. At 910, the example 900 can include identifying a period or duration corresponding to a reduced metabolic demand of a subject. Identifying the period can include using information about, among other things, a subject physical activity level or time of day, such as to identify a subject sleep state. In an example, the period of reduced metabolic demand can be indicated manually, such as by a subject or clinician, such as using the external device 120 to communicate with the IMD 105 to indicate that physiologic subject data can be collected. One or more of the implanted and/or external electrodes 202 or the physiologic signal sensor 201 can be used to receive information that can indicate whether a subject is asleep or in a relaxed state.

At 920, information indicative of one or more subject cardiac intervals can be obtained. The information can be obtained during a period corresponding to the reduced metabolic demand identified at 910. In an example, the information can include subject heart rate information. In an example, the information can include subject systolic interval information, such as including QRS information or heart sound information. The information can include R-S2 interval information, such as can be used to provide information about a subject heart rate.

At 930, a characteristic minimum can be identified using the information obtained at 920. A characteristic minimum can include, among other things, a minimum subject heart rate or a lower percentile subject heart rate, such as over a specified duration, or an absolute minimum. In an example, a characteristic minimum can include a minimum subject heart rate (or maximum cardiac interval) that can be received using the physiologic interval sensing circuit 210 over a specified duration that corresponds to reduced or minimum subject physical activity level, such as a subject sleep period.

At 940, a CHF event predictor can be determined or provided using the characteristic minimum identified at 930. In an example, the CHF event predictor can be determined using the processor circuit 110 or other processor in the system 100. In an example, a CHF event predictor can be used to identify worsening heart failure, and optionally a subject therapy can be initiated or adjusted, such as by the processor circuit 110, in response to the CHF event predictor value. In an example, in response to a CHF event predictor that indicates worsening heart failure, a lower rate limit of the IMD 105 can be raised, such as temporarily to alleviate symptoms. In an example, in response to worsening heart failure, a pacing therapy characteristic can be changed. For example, a pacing therapy signal amplitude or signal waveform shape can be changed.

Figure 10:
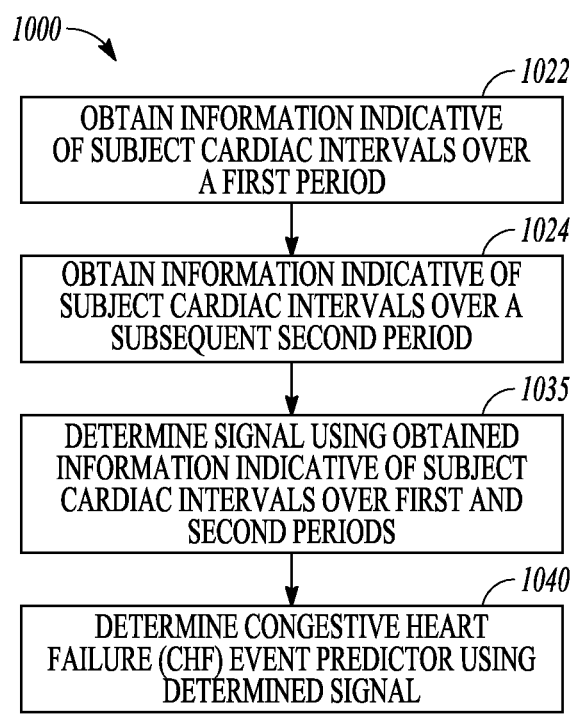
FIG. 10 illustrates generally an example that can include determining a congestive heart failure event predictor.

FIG. 10 illustrates generally an example 1000 that can include determining a CHF event predictor using information about cardiac intervals from multiple different periods. At 1022, the example 1000 can include obtaining information indicative of subject cardiac intervals over a first period. In an example, the first period can correspond to one or more night-time periods, such as over the course of a single day or multiple days. In an example, the first period can correspond to the long-term window 610 in the example of FIG. 6.

At 1024, the example 1000 can include obtaining information indicative of subject cardiac intervals over a subsequent second period. In an example, the second period can correspond to one or more night-time periods, such as over the course of a single day or multiple days. In an example, the second period can correspond to the short-term window 620 in the example of FIG. 6.

At 1035, the example 1000 can include determining an information signal using the information obtained at 1022 and 1024. The information signal can include, among other things, a characteristic or a statistical measure of the information indicative of the subject cardiac intervals corresponding to the first and second periods. As described above in the discussion of FIG. 6, among other places, the information signal can include a difference between average interval information corresponding to each of the first and second periods. The information signal can include a slope corresponding to interval information from one or both of the first and second periods.

At 1040, a CHF event predictor can be determined or provided using the signal determined at 1035. In an example, the CHF event predictor can be determined using the processor circuit 110 or other processor in the system 100. In an example, the CHF event predictor can be used to identify worsening heart failure, and optionally a subject therapy can be initiated or adjusted, such as by the processor circuit 110, in response to the CHF event predictor value.

Figure 11:
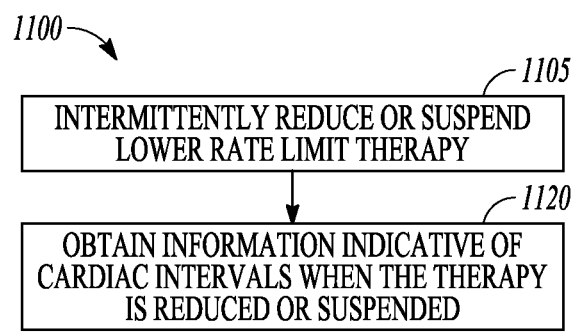
FIG. 11 illustrates generally an example that can include updating a lower rate pacing limit therapy.

FIG. 11 illustrates generally an example 1100 that can include, at 1105, intermittently or temporarily reducing or suspending a lower rate pacing limit (LRL) therapy. Reducing the LRL therapy can include reducing a lower rate pacing limit enforced by a device, for example, reducing a minimum pacing rate from 75 BPM, for example, to 70 BPM. Suspending the LRL therapy can include removing the LRL therapy such that a subject heart can operate under intrinsic or sinus control, such as for a specified duration before resuming the LRL therapy.

At 1120, the example 1100 can include obtaining information indicative of a cardiac interval when the LRL therapy is reduced or suspended, such as to obtain information about intrinsic cardiac function. Subject heart rate information can be received when the LRL therapy is suspended to identify an intrinsic subject heart rate during the suspension period.

Figure 12:
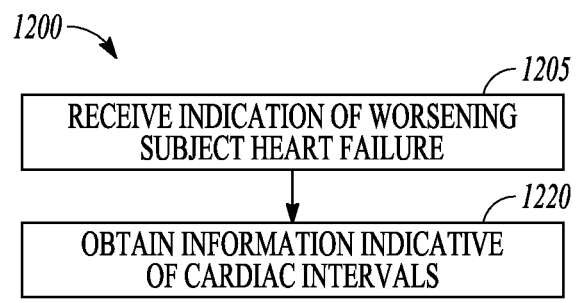
FIG. 12 illustrates generally an example that can include responding to an indication of worsening heart failure.

FIG. 12 illustrates generally an example 1200 that can include, at 1205, receiving an indication of worsening heart failure. Receiving an indication of worsening heart failure can include, among other things, receiving information about a change in a subject thoracic impedance, a change in a subject S1 or S3 heart sound characteristic, a chronically low subject physical activity level, or an increase in atrial fibrillation burden. In an example, receiving an indication of worsening heart failure can include receiving information about a subject respiratory status, such as a change in subject breathing pattern, including an increase in a subject respiratory rate, a decrease in tidal volume, an increase in rapid shallow breathing, or an increase in frequency of apnea or hypopnea episodes.

At 1220, the example 1200 can include obtaining information indicative of subject cardiac intervals. For example, when the received indication at 1205 indicates worsening heart failure, the example 1200 can include obtaining information about a subject physiologic status, such as using cardiac interval information. The information about the subject physiologic status from the cardiac interval information can be used, for example, to provide a CHF event predictor.

VARIOUS NOTES & EXAMPLES

Example 1 can include or use subject matter (such as an apparatus, a method, a means for performing acts, or a device readable medium including instructions that, when performed by the device, can cause the device to perform acts), such as can include or use congestive heart failure (CHF) event predictor method comprising obtaining information indicative of cardiac intervals over a first duration, identifying a first characteristic minimum heart rate using the information indicative of the cardiac intervals over the first duration, and determining a CHF event predictor using the identified first characteristic minimum heart rate.

Example 2 can include, or can optionally be combined with the subject matter of Example 1, to optionally include the obtaining the information indicative of the cardiac intervals over the first duration includes obtaining information about an intrinsic subject heart rate that is less than a lower rate pacing limit enforced by a cardiac rhythm management device.

Example 3 can include, or can optionally be combined with the subject matter of one or any combination of Examples 1 or 2 to optionally include the obtaining the information indicative of the cardiac intervals includes obtaining information indicative of subject systolic cardiac intervals when a lower rate pacing limit is enforced by a cardiac rhythm management device.

Example 4 can include, or can optionally be combined with the subject matter of Example 3, to optionally include the obtaining the information indicative of the subject systolic cardiac intervals includes obtaining information about subject R-S2 intervals.

Example 5 can include, or can optionally be combined with the subject matter of one or any combination of Examples 1 through 4 to optionally include receiving information indicative of a subject physical activity level, a subject posture, or a subject sleep/wake state, wherein the obtaining the information indicative of cardiac intervals corresponds to a respective one of a subject characteristic minimum physical activity level, a subject supine posture, or a subject sleep state.

Example 6 can include, or can optionally be combined with the subject matter of one or any combination of Examples 1 through 5 to optionally include receiving time-of-day information, and wherein the obtaining the information indicative of the cardiac intervals over the first duration includes using the received time-of-day information.

Example 7 can include, or can optionally be combined with the subject matter of Example 6, to optionally include the obtaining the information indicative of the cardiac intervals over the first duration includes when the received time-of-day information indicates a specified night-time duration.

Example 8 can include, or can optionally be combined with the subject matter of one or any combination of Examples 1 through 7 to optionally include the obtaining the information indicative of the cardiac intervals over the first duration includes obtaining information about an intrinsic subject heart rate that is less than a lower rate pacing limit enforced by a cardiac rhythm management device, and wherein the obtaining the information about the intrinsic subject heart rate that is less than a lower rate pacing limit includes intermittently reducing or intermittently suspending the lower rate pacing limit enforced by the cardiac rhythm management device.

Example 9 can include, or can optionally be combined with the subject matter of Example 8, to optionally include the intermittently lowering or suspending the lower rate pacing limit includes during a specified night-time duration.

Example 10 can include, or can optionally be combined with the subject matter of Example 9, to optionally include the intermittently lowering or suspending the lower rate pacing limit includes in response to a received indication of worsening heart failure.

Example 11 can include, or can optionally be combined with the subject matter of one or any combination of Examples 1 through 10 to optionally include the identifying the first characteristic minimum heart rate using the information indicative of the cardiac intervals includes calculating an average of multiple candidate minimum heart rates corresponding to the first duration.

Example 12 can include, or can optionally be combined with the subject matter of one or any combination of Examples 1 through 11 to optionally include obtaining information indicative of cardiac intervals over a second subsequent duration, identifying a second characteristic minimum heart rate using the information indicative of the cardiac intervals over the second subsequent duration, wherein the determining the CHF event predictor includes using the identified first and second characteristic minimum intrinsic heart rates.

Example 13 can include, or can optionally be combined with the subject matter of Example 12, to optionally include the determining the CHF event predictor includes using rate of change information about the first characteristic minimum intrinsic heart rate relative to the second characteristic minimum intrinsic heart rate.

Example 14 can include, or can optionally be combined with the subject matter of one or any combination of Examples 1 through 13 to optionally include obtaining information indicative of cardiac intervals over a second subsequent duration, the second subsequent duration including one or more night-time durations, identifying one or more second characteristic minimum heart rates using the information indicative of the cardiac intervals over the second subsequent duration, wherein the obtaining the information indicative of the cardiac intervals over the first duration includes obtaining the information over multiple-night time durations preceding the second subsequent duration, and wherein the determining the CHF event predictor includes using the identified first and second characteristic minimum intrinsic heart rates.

Example 15 can include or use subject matter (such as an apparatus, a method, a means for performing acts, or a device readable medium including instructions that, when performed by the device, can cause the device to perform acts), such as can include or use a processor circuit and a physiologic interval sensing circuit configured to receive information indicative of cardiac intervals over a first duration. The processor circuit can be configured to identify a first characteristic minimum of a subject heart rate using the received information indicative of the cardiac intervals over the first duration, and determine a congestive heart failure (CHF) event predictor using the identified first characteristic minimum of the subject heart rate.

Example 16 can include, or can optionally be combined with the subject matter of Example 15, to optionally include a therapy output circuit coupled to the processor circuit and configured to generate a subject therapy, the therapy output circuit coupleable to a therapy delivery electrode. In Example 16, the therapy output circuit can be configured to update a subject cardiac therapy or a subject neural electrostimulation therapy when the determined CHF event predictor indicates an increased likelihood of a subject CHF event.

Example 17 can include, or can optionally be combined with the subject matter of one or any combination of Examples 15 or 16 to optionally include an implantable medical device that includes the processor circuit and the physiologic interval sensing circuit, and an external device in data communication with the implantable medical device, wherein the external device is configured to generate a subject or clinician alert when the CHF event predictor indicates an increased likelihood of the subject CHF event.

Example 18 can include, or can optionally be combined with the subject matter of one or any combination of Examples 15 through 17 to optionally include the processor circuit configured to temporarily suspend or decrease a lower rate pacing limit for a subject cardiac rhythm management therapy during a specified night-time interval, and wherein the physiologic interval sensing circuit is configured to receive the information indicative of the cardiac intervals over the first duration corresponding to the specified night-time interval.

Example 19 can include or use subject matter (such as an apparatus, a method, a means for performing acts, or a device readable medium including instructions that, when performed by the device, can cause the device to perform acts), such as can include or use a congestive heart failure (CHF) event predictor method. Example 19 can include obtaining information indicative of cardiac intervals over a first duration, including obtaining information indicative of subject systolic intervals over the first duration, identifying a first characteristic subject systolic interval duration trend using the information indicative of the subject systolic intervals over the first duration, and determining a CHF event predictor using the identified characteristic subject systolic interval duration trend.

Example 20 can include, or can optionally be combined with the subject matter of Example 19, to optionally include the determining the CHF event predictor includes identifying a decreasing characteristic subject systolic interval duration. Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A congestive heart failure (CHF) event predictor method comprising:
   obtaining information indicative of cardiac intervals of a heart when a cardiac rhythm management device enforces a lower rate pacing limit for the heart;
   identifying a first characteristic minimum heart rate using the information indicative of the cardiac intervals obtained when the cardiac rhythm management device enforces the lower rate pacing limit; and
   determining a CHF event predictor using the identified first characteristic minimum heart rate.

2. The method of claim 1, wherein the obtaining the information indicative of the cardiac intervals includes obtaining information about an intrinsic subject heart rate that is less than the lower rate pacing limit enforced by the cardiac rhythm management device.

3. The method of claim 1, wherein the obtaining the information indicative of the cardiac intervals includes obtaining information indicative of subject systolic cardiac intervals when the lower rate pacing limit is enforced by the cardiac rhythm management device.

4. The method of claim 3, wherein the obtaining the information indicative of the subject systolic cardiac intervals includes obtaining information about subject R-S2 intervals.

5. The method of claim 1, comprising receiving information indicative of a subject physical activity level, a subject posture, or a subject sleep/wake state, wherein the obtaining the information indicative of cardiac intervals corresponds to a respective one of a subject characteristic minimum physical activity level, a subject supine posture, or a subject sleep state.

6. The method of claim 1, comprising receiving time-of-day information, and wherein the obtaining the information indicative of the cardiac intervals includes using the received time-of-day information.

7. The method of claim 6, wherein the obtaining the information indicative of the cardiac intervals includes when the received time-of-day information indicates a specified night-time duration.

8. The method of claim 2, wherein the obtaining the information about the intrinsic subject heart rate that is less than the lower rate pacing limit includes intermittently reducing or intermittently suspending the lower rate pacing limit enforced by the cardiac rhythm management device.

9. The method of claim 8, wherein the intermittently lowering or suspending the lower rate pacing limit includes during a specified night-time duration.

10. The method of claim 9, wherein the intermittently lowering or suspending the lower rate pacing limit includes in response to a received indication of worsening heart failure.

11. The method of claim 1, wherein the identifying the first characteristic minimum heart rate using the information indicative of the cardiac intervals includes calculating an average of multiple candidate minimum heart rates corresponding to the first duration.

12. The method of claim 1, comprising:
    identifying a second characteristic minimum heart rate using the information indicative of the cardiac intervals from a subsequent duration;
    wherein the determining the CHF event predictor includes using the identified first and second characteristic minimum heart rates.

13. The method of claim 12, wherein the determining the CHF event predictor includes using rate of change information about the first characteristic minimum heart rate relative to the second characteristic minimum heart rate.

14. The method of claim 1, comprising:
    obtaining information indicative of cardiac intervals over a subsequent duration, the subsequent duration including one or more night-time durations;
    identifying one or more second characteristic minimum heart rates using the information indicative of the cardiac intervals over the subsequent duration;
    wherein the obtaining the information indicative of the cardiac intervals over the first duration includes obtaining the information over multiple-night time durations preceding the subsequent duration; and
    wherein the determining the CHF event predictor includes using the identified first and second characteristic minimum heart rates.

15. A system comprising:
    a processor circuit; and
    a physiologic interval sensing circuit configured to receive information indicative of cardiac intervals of a heart when a cardiac rhythm management device enforces a lower rate pacing limit for the heart;

wherein the processor circuit is configured to:

identify a first characteristic minimum of a subject heart rate using the received information indicative of the cardiac intervals of the heart when the cardiac rhythm management device enforces the lower rate pacing limit for the heart; and determine a congestive heart failure (CHF) event predictor using the identified first characteristic minimum of the subject heart rate.

16. The system of claim 15, comprising a therapy output circuit coupled to the processor circuit and configured to generate a subject therapy, the therapy output circuit coupleable to a therapy delivery electrode;

wherein the therapy output circuit is configured to update a subject cardiac therapy or a subject neural electrostimulation therapy when the determined CHF event predictor indicates an increased likelihood of a subject CHF event.

17. The system of claim 15, comprising:

an implantable medical device that includes the processor circuit and the physiologic interval sensing circuit; and an external device in data communication with the implantable medical device, wherein the external device is configured to generate a subject or clinician alert when the CHF event predictor indicates an increased likelihood of the subject CHF event.

18. The system of claim 15, wherein the processor circuit is configured to temporarily suspend or decrease the lower rate pacing limit for a subject cardiac rhythm management therapy during a specified night-time interval, and wherein the physiologic interval sensing circuit is configured to receive the information indicative of the cardiac intervals over the specified night-time interval.

19. A congestive heart failure (CHF) event predictor method comprising:

obtaining information indicative of cardiac intervals over a first duration, including obtaining information indicative of subject systolic intervals of a heart when a cardiac rhythm management device enforces a lower rate pacing limit for the heart;

identifying a first characteristic subject systolic interval duration trend using the information indicative of the subject systolic intervals obtained when the cardiac rhythm management device enforces the lower rate pacing limit; and determining a CHF event predictor using the identified characteristic subject systolic interval duration trend.

20. The method of claim 19, wherein the determining the CHF event predictor includes identifying a decreasing characteristic subject systolic interval duration.

* * * * *